US00PP09295P

United States Patent [19]

van Andel

[11] Patent Number: Plant 9,295

[45] Date of Patent: Sep. 19, 1995

[54] POT FREESIA VARIETY NAMED 'VAPOSU'

[75] Inventor: Jacob van Andel, Aalsmer, Netherlands

[73] Assignee: Van Staaveren B.V., Aalsmeer, Netherlands

[21] Appl. No.: 331,037

[22] Filed: Oct. 28, 1994

[51] Int. Cl.[6] ..... A01H 5/00

[52] U.S. Cl. ..... Plt./83

[58] Field of Search ..... Plt. 83

*Primary Examiner*—James R. Feyrer

*Attorney, Agent, or Firm*—Christie, Parker & Hale

[57] ABSTRACT

A new variety of pot freesia suitable for growing indoors as a potted plant.

1 Drawing Sheet

BACKGROUND OF THE INVENTION

This invention relates to a new and distinct variety of Freesia which originated by crossing two unpatented, unnamed varieties of this creation at the Van Staaveren b.v. Nursery in Aalsmeer the Netherlands. The female parent is identified as 86429-AP1 and the male parent is identified as 86411-AP1. The varietal demonination of the new variety is VAPOSU.

SUMMARY OF THE INVENTION

Among the features which distinguish the new variety from other presently available and known commercial cultivars are the following combinations of characteristics: attractive off-white flowers, a habit of growth which distinguishes the new variety as a plant suitable for growing in pots and referred to as a Pot freesia variety reflecting its natural dwarf characteristics without need of growth retardants, and its ability to flower independent of soil temperature up to about 23° C. in about 80 to about 110 days.

Asexual reproduction of the new variety vegetatively by corms and cormlets in Aalsmeer, Netherlands show the foregoing and other distinguishing characteristics are transmitted through succeeding generations.

BRIEF DESCRIPTION OF ILLUSTRATION

The accompanying photograph illustrates the new variety and shows the flowering thereof from bud to full bloom depicted in color as nearly correct as it is possible to make in a color illustration of this character. Throughout this description, color values are based upon the Colour Chart of The Royal Horticultural Society of London, England, except where common terms of color definition are employed.

DESCRIPTION OF THE NEW VARIETY

The following description is of Pot Freesia Plants of the new cultivar grown under glass in Aalsmeer, Netherlands, during the months of August and September. Phenotyphic expression may vary with environment, cultural and climatic conditions, as well as differences and conditions in light, soil, and temperature.

PLANT

A. Form: Upright.

B. Growth:

*Height attained.*—Depending on temperature about 35 cm– about 45 cm. The higher the temperature, the more leaves the plant produces and the longer they are at higher temperatures, the more buds are produced in a spike. The lower the light intensity the longer and weaker are the leaves. Each combination of temperature and light intensity has a special formative influence on plant shape. Measurements given herein were made on plants grown initially at 12° C. and up to 24° C. at flowering time. Generally, The cooler the plants are grown, the more compact the plants will grown and the more days that are necessary between planting and flowering.

*Branching.*—The flower stalk bears 1 or 2 short side shoots with flower buds.

C. Flower stem:

1. *Length.*—Depending on temperature about 35 cm to about 45 cm.
2. *Color.*—Medium green, surface rough.

D. Foliage:

1. *Quantity.*—Five to eight leaves per item depending on temperature.
2. *Size.*—Length: about 35 cm to about 45 cm; Width: about 1 cm to about 3 cm (depends on temperature and light intensity).
3. *Shape.*—Oblong with entire margins.
4. *Texture.*—Smooth.
5. *Color.*—Near 146 A/B.
6. *Veination.*—Fressia-like.
7. *Stem color.*—Near to 146A.
8. *Corms.*—Color: White with brown scales. Size: Varying with age, to 80 mm circumference.

THE BUD STAGE

Bud form (shape): Long, ovate.

Bud size (dimensions): Length about 40 mm to about 45 mm; diameter about 15 mm.

Opening rate: Medium.

Color:

*When petals first divide.*—155 D.

*When petals begin to unfurl.*—155 D.

Calyx: Tubular, smooth.

Size: Small.

THE FLOWER STAGE

Blooming habit: Intermittent, once early.

Form: Freesia-like.

Approximate number of flowers: 7 to 9 per spike.

Borne: In a spike.

Size (fully expanded):

*Diameter.*—About 45 mm.

*Depth.*—About 55 to 65 mm.

Shape: Cup shaped.

Color tonality from a distance: White.

Lasting quality (days) on plant: Each flower about 15 to about 20 days, depends on temperature.

Flower color:

*Describe flower coloration.*—Main color of innerside of the lateral outer tips near 155A.

*Inner petals.*—Main color of innerside of the medium outer tips, near 155A and near 23A; main color of innerside of the lateral inner tips, near 155A and near 23A.

*Outer petals.*—Main color of innerside of the lateral inner tips, near 155A.

*Discoloration as bloom ages.*—Flower color becomes a darker shade to pale light brown.

*Petals.*—Number of petals — 6. Arrangement — Tubular imbricated.

*Texture.*—Soft.

*Shape.*—6 tips to a tube.

*Persistence (No. of days) on plant.*—About 15 to about 20 days.

*Fragrance.*—Faintly salty.

REPRODUCTIVE ORGANS

Stamens: White.

Color: White just before opening.

Pollen (color): White.

Pistils: White.

*Styles.*—White.

*Stigmas.*—White.

I claim:

1. A new and distinct variety of pot freesia substantially as described and illustrated herein.

* * * * *

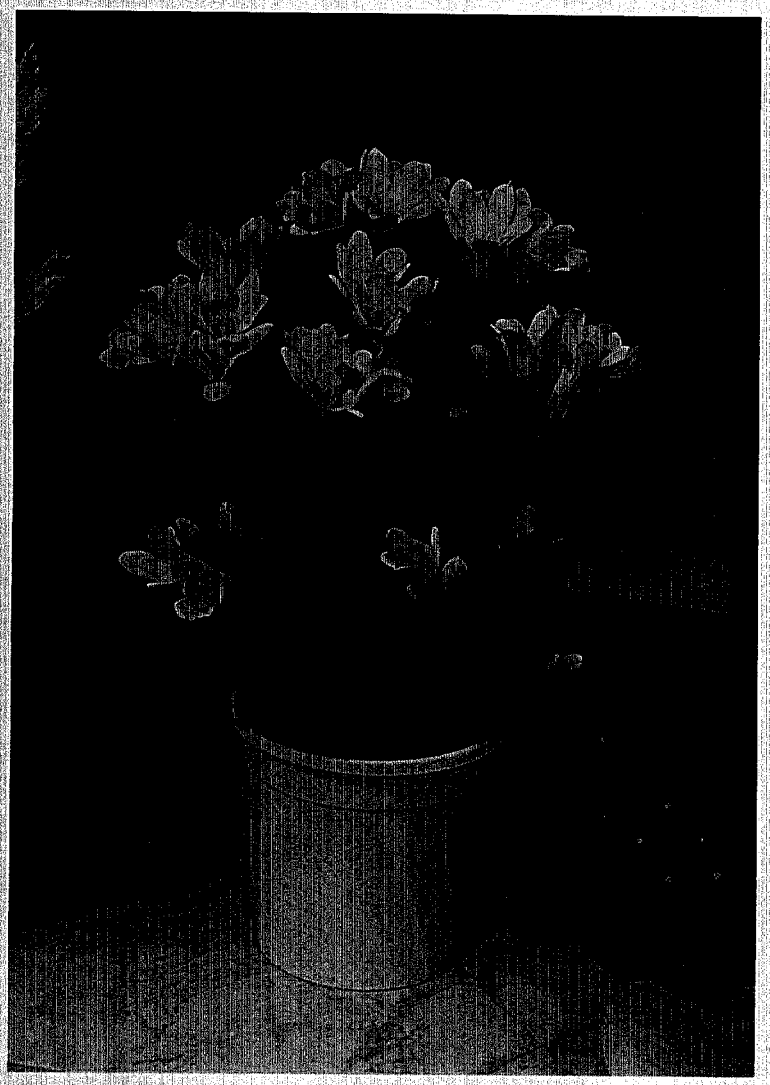

UNITED STATES PATENT AND TRADEMARK OFFICE

CERTIFICATE OF CORRECTION

PATENT NO. : Plant 9,295

DATED : September 19, 1995

INVENTOR(S) : Jacob van Andel

It is certified that error appears in the above-indentified patent and that said Letters Patent is hereby corrected as shown below:

Column 2, line 10, change "grown" to -- grow --.

Signed and Sealed this

Second Day of April, 1996

*Attest:*

Bruce Lehman

BRUCE LEHMAN

*Attesting Officer*

*Commissioner of Patents and Trademarks*